US012042385B2

United States Patent
Saadatmanesh et al.

(10) Patent No.: US 12,042,385 B2
(45) Date of Patent: Jul. 23, 2024

(54) COMPOSITIONS AND METHODS FOR TREATING BONE FRACTURES

(71) Applicant: ARIZONA BOARD OF REGENTS ON BEHALF OF THE UNIVERSITY OF ARIZONA, Tucson, AZ (US)

(72) Inventors: Hamid Saadatmanesh, Tucson, AZ (US); Mehrnoosh Zarkoob, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 0 days.

(21) Appl. No.: 18/185,172

(22) Filed: Mar. 16, 2023

(65) Prior Publication Data
US 2023/0218400 A1    Jul. 13, 2023

Related U.S. Application Data

(63) Continuation of application No. 17/630,077, filed as application No. PCT/US2020/043373 on Jul. 24, 2020.
(Continued)

(51) Int. Cl.
*A61F 2/28* (2006.01)
*A61L 27/08* (2006.01)
(Continued)

(52) U.S. Cl.
CPC .............. *A61F 2/2846* (2013.01); *A61F 2/28* (2013.01); *A61L 27/08* (2013.01); *A61L 27/54* (2013.01); *A61L 27/56* (2013.01); *A61F 2002/2839* (2013.01); *A61F 2002/30677* (2013.01); *A61F 2002/3084* (2013.01);
(Continued)

(58) Field of Classification Search
CPC .. A61F 2/2846; A61F 2/28; A61F 2002/2839; A61F 2002/30677; A61F 2002/3084; A61F 2002/30919; A61F 2310/00155; A61F 2310/00161; A61F 2310/00574; A61F 2/30965; A61F 2002/2825; A61F 2002/2835; A61F 2002/307; A61L 27/08; A61L 27/54; A61L 27/56; A61L 2300/404; A61B 17/7258; A61B 17/72
See application file for complete search history.

(56) References Cited

U.S. PATENT DOCUMENTS 5,181,930 A * 1/1993 Dumbleton ............. B29C 70/86
                                                  623/23.34
6,425,923 B1   7/2002 Stalcup
(Continued)

OTHER PUBLICATIONS

Pandey et al. "Some biocompatible materials used in medical practices—a review." International journal of pharmaceutical sciences and research 7.7 (2016): 2748-2755.

*Primary Examiner* — Yashita Sharma
(74) *Attorney, Agent, or Firm* — NGUYEN TARBET LLC (57) ABSTRACT

Provided herein are compositions and methods for treating bone fractures. In particular, provided herein are systems comprising carbon fiber sleeves and biocompatible polymers and the use of such systems in treating or preventing bone fractures.

9 Claims, 4 Drawing Sheets

Related U.S. Application Data (60) Provisional application No. 62/878,484, filed on Jul. 25, 2019.

(51) Int. Cl.
*A61L 27/54* (2006.01)
*A61L 27/56* (2006.01)
*A61F 2/30* (2006.01)

(52) U.S. Cl.
CPC ............... *A61F 2002/30919* (2013.01); *A61F 2310/00155* (2013.01); *A61F 2310/00161* (2013.01); *A61F 2310/00574* (2013.01); *A61L 2300/404* (2013.01)

(56) References Cited

U.S. PATENT DOCUMENTS

| | | |
|---|---|---|
| 6,759,352 B2 | 7/2004 | Delanoy et al. |
| 7,041,192 B2 | 5/2006 | Delanoy et al. |
| 7,806,900 B2 | 10/2010 | Rabiner |
| 9,320,601 B2 | 4/2016 | D'Agostino et al. |
| 10,028,776 B2 | 7/2018 | D'Agostino et al. |
| 10,517,654 B2 | 12/2019 | D'Agostino et al. |
| 2003/0001825 A1 | 1/2003 | Omura et al. |
| 2005/0043733 A1 | 2/2005 | Eisermann et al. |
| 2010/0076503 A1 | 3/2010 | Beyar et al. |
| 2010/0114097 A1 | 5/2010 | Siravo et al. |
| 2010/0268232 A1 | 10/2010 | Betz et al. |
| 2013/0253661 A1 | 9/2013 | D'Agostino et al. |

\* cited by examiner

Double Layered Sleeve

Inner Non-Porous Sleeve

Outer Controlled Porous Sleeve

FIG. 4

COMPOSITIONS AND METHODS FOR TREATING BONE FRACTURES

CROSS-REFERENCE TO RELATED APPLICATIONS

This application is a continuation and claims benefit of U.S. application Ser. No. 17/630,077 filed Jan. 25, 2022, which is a 371 of PCT/US2020/043373 filed Jul. 24, 2020, which claims benefit of U.S. Provisional Patent Application No. 62/878,484, filed Jul. 25, 2019, the specification(s) of which is/are incorporated herein in their entirety by reference.

FIELD OF THE INVENTION

Provided herein are compositions and methods for treating and stabilizing bone fractures. In particular, provided herein are systems comprising fiber sleeves and biocompatible polymers and the use of such systems in treating bone fractures.

BACKGROUND OF THE INVENTION

A bone fracture is a medical condition where the continuity of the bone is broken. A significant percentage of bone fractures occur because of high force impact or stress. However, a fracture may also be the result of medical conditions that weaken the bones, for example osteoporosis, some cancers, or osteogenesis imperfecta.

Bone healing is a process which in most cases occurs naturally. Fracture treatment is usually aimed at making sure there is the best possible function of the injured part after healing. Treatment also focuses on providing the injured bone with the best circumstances for optimum healing (e.g., immobilization with internal or external stabilization). For the natural healing process to begin, the ends of the broken bone need to be lined up; this is known as reducing the fracture. Fracture reduction may be done by manipulation, closed reduction (pulling the bone fragments), or surgery.

As soon as the bones are aligned, they must stay aligned while they heal. This may include: plaster casts or plastic functional braces that these hold the bone in position until it has healed; metal plates and screws that may use minimally invasive techniques; intra-medullary nails, which are internal metal rods or flexible wire that are placed down the center of long bones; and external fixators made of metal or carbon fiber that have steel pins that go into the bone directly through the skin.

Usually, the fractured bone area is immobilized for 2-8 weeks. The duration depends on which bone is affected and whether there are any complications, such as a blood supply problem or an infection.

Improved methods for aligning and immobilizing and stabilizing fractures and preventing fractures in bones at risk of fracture are needed.

SUMMARY OF THE INVENTION

Almost all major bone fractures require some form of incision to allow bone alignment and attachment of stabilizing rods, brackets, etc. Such incisions typically create significant trauma and require extensive rehabilitation time.

U.S. Pat. No. 6,425,923 describes an orthopedic implant that includes a flexible bag having at least a portion thereof which is expandable under pressure; and a polymer within the bag. The orthopedic implant is implanted within a bone by forming a cavity in the bone; inserting a flexible bag into the cavity, the flexible bag having at least a portion thereof which is expandable under pressure; pressure filling the bag with a polymer, whereby the expandable portion of the bag expands to substantially entirely fill the cavity in the bone; and hardening the polymer. In addition, U.S. Pat. App. No. 20100076503 describes a method of long bone strengthening and a composite implant for such strengthening (e.g., a plurality of rigid tensile rods, in matrix of cement and surrounded by a partially porous bag). However, these, and other existing solutions fail to meet the need for a bone repair, strengthening system, and an infection prevention system that is permanent (e.g., non-absorbable), while providing the option for removal and further fail to provide a customizable solution for each patient's need.

Provided herein is an improved method that eliminates the need for any incision or internal containment bag and utilizes no dissolvable or absorbable material and resists infection. The method includes insertion of an ultra-thin, braided, woven, or prepreg carbon fiber tube inside the bone cavity followed by the injection of a biocompatible polymer inside the carbon fiber tube. In this manner, a very strong dowel (e.g., ten times stronger than steel) is created inside the bone cavity bridging the sides of the fracture. The systems and methods described herein eliminate the need for open cuts and result in significantly less trauma and recovery time. In addition, the lack of metal eliminates potential interference issues with imaging techniques such as MRI. The systems and methods described herein provide a non-absorbable solution for repair and strengthening of bones that can be left in place permanently or removed if desired.

For example, in some embodiments, provided herein is a method of treating or stabilizing (e.g., by strengthening a bone) a bone fracture or strengthening a bone in a subject, comprising: a) making at least one (e.g., 1, 2, 3, 4, or more) holes (e.g., on the mm scale in diameter) through a bone, wherein optionally a first of hole is placed on the proximal side of the bone fracture and an optional second hole is on the distal side of the bone fracture; and b) inserting a tube (e.g., carbon fiber tube) into a first hole (e.g., optionally between the first and second holes); and optionally c) filling the tube with a biocompatible polymer. In some embodiments, the holes are drilled (e.g., using laparoscopy). In some embodiments, the tube is a double layer carbon fiber tube. In some embodiments, inserting the carbon fiber tube comprises the steps of inserting the carbon fiber tube in the first hole and drawing the carbon fiber tube via a lead wire that exits the second hole. In some embodiments, the subject has a fracture. In some embodiments, the subject is at increased risk of a fracture (e.g., due to overuse, injury, or disease (e.g., osteoporosis). In some embodiments, the fiber tube is permanently placed in the bone. In some embodiments, the fiber tube is removable (e.g., by activating a depolymerization agent). In some embodiments, the fiber tube is configured to resist compressive, torsional, and shear forces when placed in a bone. In some embodiments, at least a portion of the fiber tube conforms to the shape of a bone cavity in the bone or retains a tube shape after placement in the bone.

The present disclosure is not limited to a particular material or configuration of carbon or other fiber tube. In some embodiments, the carbon fiber tube is ultrathin layer of carbon fabric. In some embodiments, the carbon fiber tube is a multi (e.g., double) layer bag comprising outer and inner carbon fiber layers. In some embodiments, the outer carbon fiber layer is porous and the inner carbon fiber layer is non-porous. In some embodiments, the fiber tube comprises one or more surface modifications (e.g., electrochemical, chemical, thermal, discharge plasma, or radiation treatment). In some embodiments, the surface modifications comprise or are antimicrobial agents (e.g., cationic groups such as quaternary ammonium compounds, metal-based antimicrobials such as silver or bismuth, polymer-based antimicrobials such as polyhexamethylene biguanide and or oxidizing agents such as hydrogen peroxide. In some embodiments, the carbon fiber tube is pre-impregnated with a resin system that polymerizes at a service temperature (e.g., a temperature lower than body temperature). In some embodiments, the impregnated sleeve is kept at lower than body temperature and when it is inserted in the body it will start to polymerize at the body temperature, which is higher than the storage temperature. In some embodiments, the resin polymerizes after insertion of the carbon fiber sleeve in the bone.

The present disclosure is not limited to a particular biocompatible polymer. In some embodiments, the biocompatible polymer is calcium phosphate, poly(lactic-co-glycolic) acid, polyanhydrides, polyvinylchloride (PVC), polyethylene (PE), polypropylene (PP), polymethylmetacrylate (PMMA), polystyrene (PS), polytetrafluoroethylene (PTFE), polyurethane (PU), polyamide (nylon), polyethylenterephthalate (PET), polyethersulfone (PES), polycarbonates (PC), and polyetherimide (PEI), Polycaprolactone (PCL), or mineralized bone particles (MBP). In some embodiments, the biocompatible polymer comprises a depolymerization agent (e.g., gold nanoparticles or a degradable crosslinker (e.g., 1,4-diacetylbenzene 1,4-bis(O-methacryloyl)dioxime or 1,3,5-triacetylbenzene 1,3,5-tris(O-methacryloyl)trioxime)). In some embodiments, the polymer is pre-compressed before filling. In some embodiments, the polymer is an expansive polymer (e.g., functionalized with crosslinkers for in situ polymerization). In some embodiments, the biocompatible polymer is injected into the fiber tube. In some embodiments, the biocompatible polymer comprises a carbon fiber reinforcing component (e.g., including but not limited to, carbon fiber spring or flexible internal scaffold). In some embodiments, at least one physical property of the biocompatible polymer is altered based on external stimulus (e.g., electrical or physical stimulus).

In some embodiments, the fiber tube and/or biocompatible polymer further comprise an active agent. In some embodiments, the active agent is an antimicrobial agent, a drug (e.g., antibiotic, chemotherapeutic agent, or an agent that promotes bone healing (e.g., growth factor) or bone precursor (e.g., osteoblast or osteoclast).

Further embodiments provide a kit or system, comprising: a fiber tube; and a biocompatible polymer and optionally an implant retrieval system. In some embodiments, the kit or system further comprises one of more of a guide wire and/or a carbon fiber reinforcing component.

Additional embodiments provide a kit or system as described herein for use in treating a bone fracture or strengthen a bone (e.g., in a subject at risk of a fracture (e.g., a subject with overuse, a bone injury, or disease (e.g., osteoporosis or cancer)).

Additional embodiments provide the use of a kit or system described herein for to treat a bone fracture or strengthen a bone (e.g., in a subject at risk of a fracture (e.g., a subject with overuse, a bone injury, or disease (e.g., osteoporosis or cancer)).

The present disclosure is not limited to the treatment of a particular type of fracture. Examples include, but are not limited to, stable fractures, open, compound fractures, transverse fractures, oblique fractures, and comminuted fractures of the clavicle, sternum, phalanges, metacarpals, radius, ulna, hip, femur, tibia, or fibula. In some embodiments, the subject has osteoporosis.

The present disclosure is not limited to a particular subject. In some embodiments, the subject is a human or non-human animal (e.g., horse or companion animal).

Additional embodiments are described herein.

DESCRIPTION OF THE DRAWINGS

The features and advantages of the present invention will become apparent from a consideration of the following detailed description presented in connection with the accompanying drawings in which.

DEFINITIONS

To facilitate an understanding of the present invention, a number of terms and phrases are defined below:

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human or non-subject.

As used herein, the term "non-human animals" refers to all non-human animals including, but not limited to, vertebrates such as rodents, non-human primates, ovines, bovines, ruminants, lagomorphs, porcines, caprines, equines, canines, felines, ayes, etc.

"Polymer" is any natural or synthetic molecule which can form long molecular chains, such as polyolefin, polyamides, polyesters, polyurethanes, polypeptides, polysaccharides, and combinations thereof.

A "biocompatible polymer" is a polymer that does not produce toxins or harmful products and preferably does not stimulate an immune response in biological systems. Biocompatible polymers may be natural or synthetic.

DETAILED DESCRIPTION OF THE INVENTION

Provided herein are improved systems and methods for bone healing. The systems and methods described herein are minimally invasive and provide strong, flexible supports for healing bone breaks and support bones weakened by osteoporosis.

Figure 1:
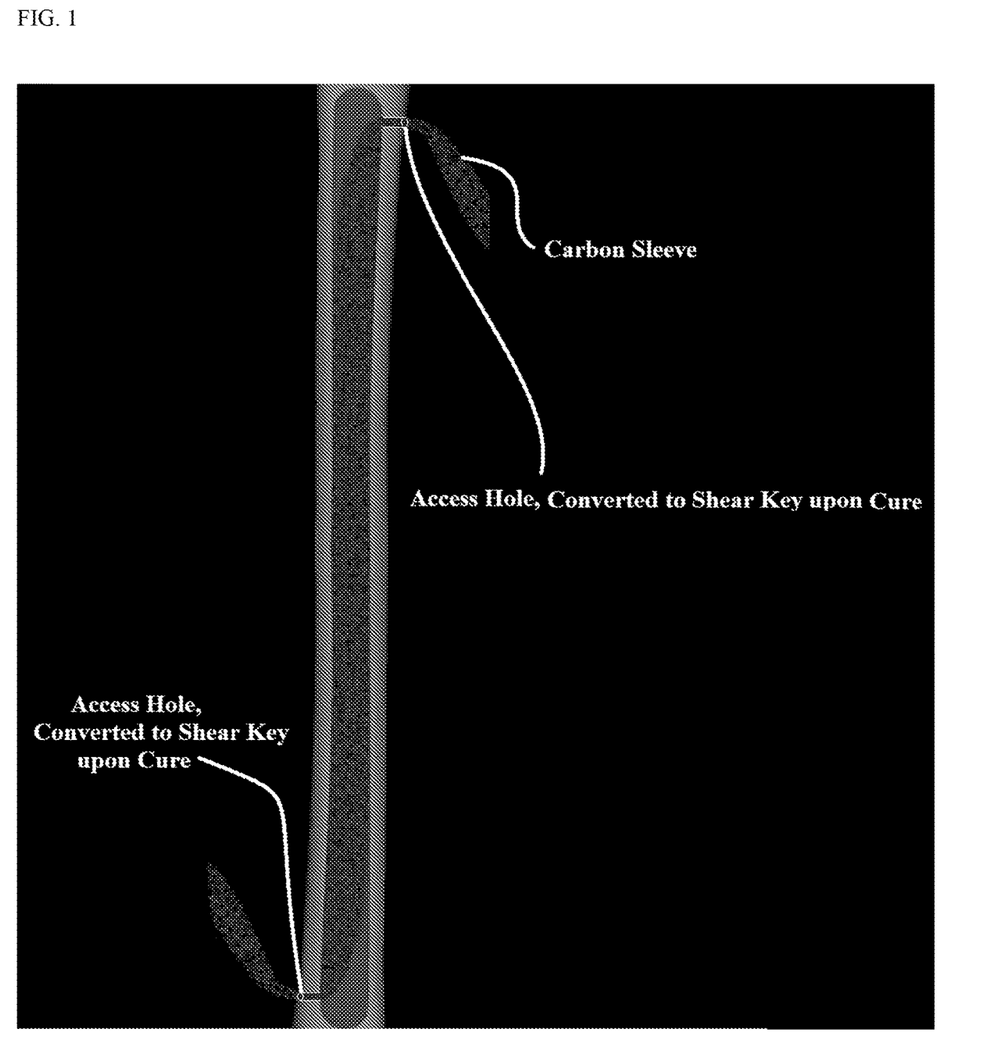
FIG. 1 shows a shear key that mechanically interlocks dowel to bone.

For example, in some embodiments, the present invention provides a method for treating fractures and/or strengthening bones. The basic procedure is as follows: first, at least one (e.g., 1, 2, 3, 4, or more) small holes (e.g., mm scale each) are drilled (e.g., laparoscopically) into and through a bone on different sides of the fracture line (e.g., horizontally, or vertically, depending on the fracture). Next, a fiber (e.g., carbon fiber) tube, sleeve, or bag is inserted into a hole. In some embodiments, the fiber tube is drawn out through a lead wire or other guide component through a second hole. In some embodiments, a biocompatible resin is then injected into the tube, expanding it to fully fill the bone cavity and creating an internal dowel bridging the two sides of the fracture line, as shown in FIG. 1. the sleeve bonds to the bone and acts as a permanent solution rather than a dissolvable and absorbable material. However, in some embodiments, the components of the system are removable if desired.

The systems and methods described herein eliminate the need for an open cut and result in significantly less trauma and recovery time than existing methods, which require an open incision. This technique is particularly effective in areas of the body where bracing cannot be provided such as, for example, fractures of the collar bone.

In some embodiments, after the access holes are filled, they act as shear keys developing a mechanical interlock between the internal hardened carbon sleeve and the bone, giving significant structural integrity to the bone/sleeve combination, as shown in FIG. 1.

The present disclosure is not limited to a particular type of carbon fiber tube or carbon fiber material. Carbon fibers (CF, graphite fiber) are fibers about 5-10 micrometers in diameter that are composed mostly of carbon atoms. Carbon fibers have several advantages including, but not limited to, high stiffness, high tensile strength, low weight, high chemical resistance, high temperature tolerance and low thermal expansion. These properties have made carbon fiber very popular in aerospace, civil engineering, military, and motorsports, along with other competition sports.

To produce a carbon fiber, the carbon atoms are bonded together in crystals that are more or less aligned parallel to the long axis of the fiber as the crystal alignment gives the fiber high strength-to-volume ratio (making it strong for its size). Several thousand carbon fibers are bundled together to form a tow, which may be used by itself or woven into a fabric.

Carbon fibers are usually combined with other materials to form a composite. When impregnated with a resin, they form carbon-fiber-reinforced polymer (often referred to as carbon fiber) which has a very high strength-to-weight ratio and is extremely rigid. Carbon fibers are also composited with other materials, such as graphite, to form reinforced carbon-carbon composites, which have a very high heat tolerance.

Carbon fiber is frequently supplied in the form of a continuous tow wound onto a reel. The tow is a bundle of thousands of continuous individual carbon filaments held together and protected by an organic coating, or size, such as polyethylene oxide (PEO) or polyvinyl alcohol (PVA). The tow can be conveniently unwound from the reel for use. Each carbon filament in the tow is a continuous cylinder with a diameter of 5-10 micrometers and is almost exclusively carbon.

The atomic structure of carbon fiber is similar to that of graphite, comprising sheets of carbon atoms arranged in a regular hexagonal pattern (graphene sheets), the difference being in the way these sheets interlock. Graphite is a crystalline material in which the sheets are stacked parallel to one another in regular fashion. The intermolecular forces between the sheets are relatively weak Van der Waals forces, giving graphite its soft and brittle characteristics.

Precursors for carbon fibers are polyacrylonitrile (PAN), rayon and pitch. Carbon fiber filament yarns are used in several processing techniques: the direct uses are for prepregging, filament winding, pultrusion, weaving, braiding, etc. Carbon fiber yarn is rated by the linear density (weight per unit length; i.e., 1 g/1000 m=1 tex) or by number of filaments per yarn count, in thousands. For example, 200 tex for 3,000 filaments of carbon fiber is three times as strong as 1,000 carbon filament yarn but is also three times as heavy. This thread can then be used to weave a carbon fiber filament fabric or cloth. The appearance of this fabric generally depends on the linear density of the yarn and the weave chosen. Some commonly used types of weave are twill, satin and plain. Carbon filament yarns can also be knitted or braided.

Each carbon filament is produced from a polymer such as polyacrylonitrile (PAN), rayon, or petroleum pitch, known as a precursor. For synthetic polymers such as PAN or rayon, the precursor is first spun into filament yarns, using chemical and mechanical processes to initially align the polymer molecules in a way to enhance the final physical properties of the completed carbon fiber. Precursor compositions and mechanical processes used during spinning filament yarns may vary among manufacturers. After drawing or spinning, the polymer filament yarns are then heated to drive off non-carbon atoms (carbonization), producing the final carbon fiber. The carbon fibers filament yarns may be further treated to improve handling qualities, then wound on to bobbins.

A common method of manufacture involves heating the spun PAN filaments to approximately 300° C. in air, which breaks many of the hydrogen bonds and oxidizes the material. The oxidized PAN is then placed into a furnace having an inert atmosphere of a gas such as argon, and heated to approximately 2000° C., which induces graphitization of the material, changing the molecular bond structure. When heated in the correct conditions, these chains bond side-to-side (ladder polymers), forming narrow graphene sheets which eventually merge to form a single, columnar filament. The result is usually 93-95% carbon. Lower-quality fiber can be manufactured using pitch or rayon as the precursor instead of PAN. The carbon becomes further enhanced, as high modulus, or high strength carbon, by heat treatment processes. Carbon heated in the range of 1500-2000° C. (carbonization) exhibits the highest tensile strength (5,650 MPa, or 820,000 psi), while carbon fiber heated from 2500 to 3000° C. (graphitizing) exhibits a higher modulus of elasticity (531 GPa, or 77,000,000 psi).

In some embodiments, commercially available carbon fiber materials are used in the described compositions and methods (e.g., available from DowAksa, LLC (Istanbul, Turkey) and Toray (Tokyo, Japan)). In some embodiments, carbon fibers for use herein comprise filaments that are produced with fiber diameters of approximately 5 microns (e.g., plus or minus 5, 10, 15, or 20%). Examples include, but are not limited to, T-700 fibers manufactured by Toray and A49 fibers manufactured by DowAksa.

Figure 4:
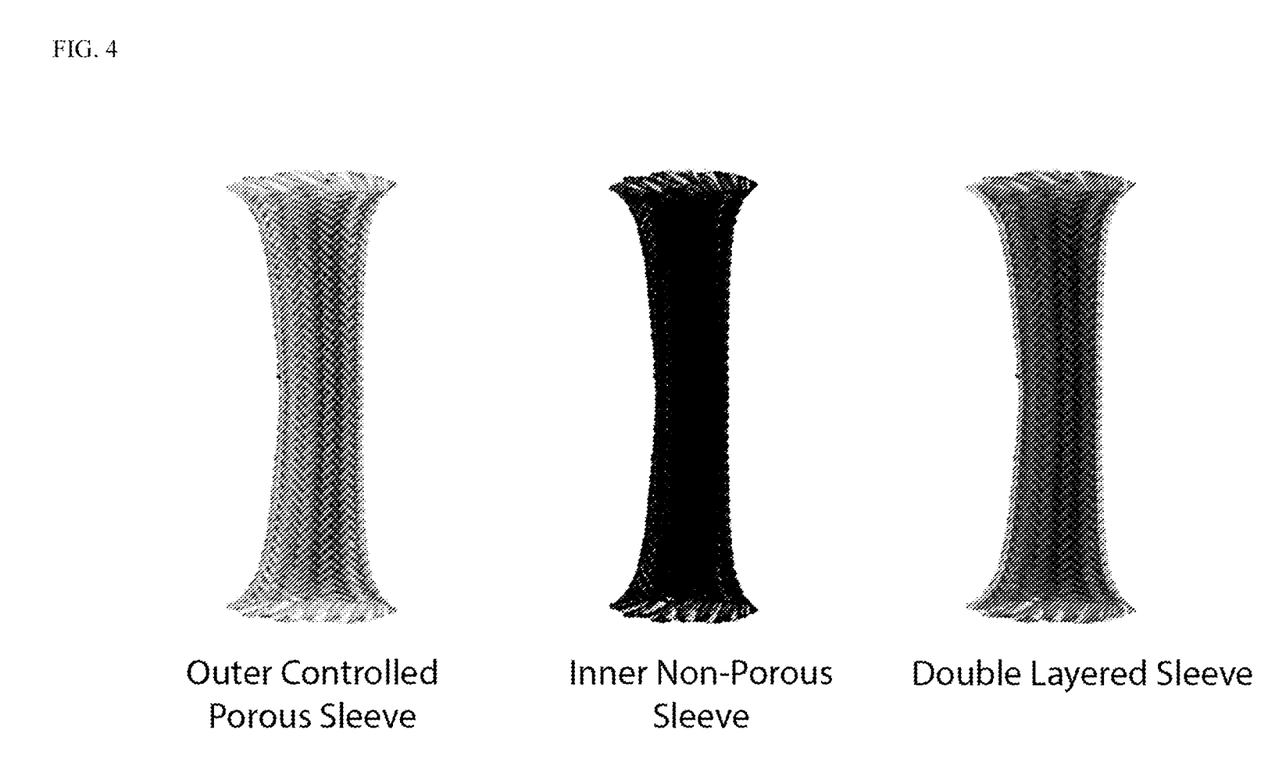
FIG. 4 shows exemplary double layered carbon sleeves.

In some embodiments, the fiber tube is impervious, permeable (e.g., braided), or with controlled porosity (e.g., as shown in FIG. 4), although the present disclosure is not limited to a particular configuration. In some embodiments, at least a portion of the fiber tube is configured to conform to the shape of the bone cavity (e.g., by using a flexible material). In some embodiments, at least a portion of the fiber tube is rigid enough to maintain a shape (e.g., tube shape) after placement in the bone cavity. In some embodiments, different segments of the fiber tube are customized to have different levels of flexibility or porosity. In this manner, the fiber tube can be customized to the shape of the bone, the type of bone, and the type of repair or strengthening desired.

In some embodiments, fiber angles in a braided tube are optimized to create a compatible stiffness to that of the bone. By designing and manipulating the angle of the fibers in the sleeve with respect to the longitudinal axis of the bone this stiffness is adjusted to match that of the bone. In some embodiments, this is performed analytically and verified experimentally. In some embodiments, the fiber tube and/or biocompatible polymer are designed to resist compressive, torsional, and shear forces while maintaining flexibility for healing and movement.

In addition to the excellent mechanical properties and biocompatibility, carbon fiber has the added benefit of acting as an antioxidant in the body. Carbon fibers have multiple advantages in developing high-strength biomaterials with a density close to bone for better stress transfer and electrical properties that enhance tissue formation. Carbon-fiber-reinforced composite has been shown to stimulate osseointegration inside the tibia bone marrow measured as percent bone area (PBA) to a great extent when compared to the titanium-6-4 alloy at statistically significant levels.

In some embodiments, multiple layers (e.g., 1, 2, 3, 4, 5 or more layers) of fiber (e.g., prepreg fiber) are implanted in the bone cavity (e.g., to create enough strength and stiffness without the need for the infill materials for repair and strengthening of the bone).

In some embodiments, the carbon fiber tube is multi (e.g., two) layered. An Exemplary double layer tube, bag, or sleeve is shown in FIG. 4. The right panel of FIG. 4 shows a double layered sleeve. In some embodiments, the carbon fiber tube is a double layer flexible bag where the outer sleeve (left panel of FIG. 4) is in apposition with the host bone and has a porous (e.g., 10 μm-200 μm pores), e.g., cationic surface and the inner sleeve (center panel of FIG. 4) is non-porous (e.g., <10 μm pores) and holds the injectable biocompatible polymer. The reduced porosity of the inner sleeve of the carbon tube serves to contain the polymer solution within the flexible bag and minimize any leakage into the medullary cavity under pressure, and also to minimize the infiltration of inflammatory cells like foreign body giant cells, macrophages and osteoclasts that can result in degradation of the polymeric implant.

In some embodiments, the carbon fiber tube has a diameter between 5 mm to 45 mm±1, 2, 3, 4, 5, or 10 mm. This size range allows for insertion of the carbon fiber tube into the medullary cavity of the bone, press-fit to the endosteal layer of the medullary cavity of the bone, and allows the optimal amount of polymer to be injected and to withstand the pressure and produce a robust internal stabilization of the fracture. In some embodiments, the size is altered to accommodate the medullary shaft of the bone, as it varies based on the anatomic location (femur, tibia, radius, ulna, clavicle, phalanges), age, sex, and disease conditions.

The present disclosure is exemplified with carbon fiber tubes. However, the present disclosure is not limited to carbon fiber tubes. Additional fibers (e.g., poly-paraphenylene terephthalamide (Kevlar), polyethylene (Spectra), etc.) are also suitable for use in the described compositions and methods.

In some embodiments, the systems and methods described herein use a prepreg carbon fiber sleeve to support bone fragments. Prepreg carbon fabric material is an ultra-thin layer of carbon fabric that is pre-impregnated with a resin system and kept at a temperature below the service temperature. As long as this temperature is maintained, the resin remains flexible and no curing reaction occurs until the fabric temperature reaches a higher temperature (e.g., service temperature). The difference between the storage and service temperatures can be manipulated to fit a special set of needs and parameters. For example, in some embodiments, a prepreg sleeve is pre-impregnated and kept at a temperature of about 5 degrees Centigrade and then implanted in the body where curing begins at body temperature. When the sleeve is placed inside the bone cavity, it bonds to the inner surface of the bone and bone fragments to form a solid load bearing structural element.

In some embodiments, instead of a fiber, a filler material comprising short chopped carbon or other fibers within the infill matrix is used. In some embodiments, the chopped carbon fibers comprise a "sizing" that matches the type of the infill polymer and the carbon fiber to create a strong chemical bond between the two materials.

In some embodiments, fiber tubes comprise sizing in order to improve bonding with the polymer fill. Polyether and polyester polyurethane dispersion based on aliphatic diisocyanates are often used to formulate polyurethane carbon fiber sizing. Electroactive Polymers (EAP) and Electrostrictive Graft Elastomers are non-liming examples of products that are used as sizing in the compositions and methods described herein. In some embodiments, the sizing on the carbon fibers cross-links with the saturating resin or the polymer infill materials to form a strong chemical bond.

In some embodiments, fiber tubes comprise surface modification (e.g., of a layer of the carbon tube or sleeve that is in contact with the host tissue). The surface modifications serve to, for example, mitigate the risk of infection of the defect. In some embodiments, this is achieved by modifying or functionalizing the outer surface of the carbon fiber with antimicrobial coatings or attaching antimicrobial agents to modified surfaces.

The present disclosure is not limited to particular surface coatings or treatments. Examples include but are not limited to, modification by electrochemical, chemical, thermal, discharge plasma, radiation treatment. In some embodiments, modification of the surface of the carbon fiber increases the wettability of the fiber surface by the matrix resin and increases interaction with the host body fluid. This increases roughness, which promotes more surface area on the fiber, and improves interactions between matrix resin and the host tissue. In some embodiments, surface modification and the porosity of the carbon tube promotes mechanical interlocking between the fiber and the host tissue and increases the number of active sites on the fiber surface for subsequent chemical bonding. For example, in some embodiments, surface treatment by chemical, plasma or radiation leads to oxidation of the surface and increases active groups (e.g., carboxyl, carbonyl, ester, lactone, enol and quinone), leading to enhanced chemical bonding with the matrix resin or host tissue. This also allows one to functionalize the carbon surface by crosslinking/grafting/co-polymerizing antimicrobial molecules or biomolecules for, for example, preventing infection and or improved osseointegration.

The surface modification of the outer layer of the carbon tube increases the active sites (e.g., functional groups) for coating/grafting/crosslinking of antimicrobial molecules or compounds. The use of cationic carbon fiber in bone further prevents infection of the implant site without using antibiotics or sensitizing the microbes to become resistant.

Surface modified carbon increases the presence of functional groups like carboxyl (COOH), carbonyl (C=O), ester (COO), lactone or cyclic carboxylic esters (—(C=O)—O—). In some embodiments, these functional groups are used to crosslink quaternary ammonium and other cationic salts via electrostatic binding or covalent crosslinking via alkylation. In some embodiments, agents are grafted using cationic photoinitiators and UV photopolymerization onto the surface of the carbon fiber. The design and development of antimicrobial carbon surface is not limited to quaternary ammonium, as other compounds such as metal based antimicrobials (e.g., silver, bismuth), polymer-based antimicrobials (e.g., polyhexamethylene biguanide—PHMB) and oxidizing agents (e.g., hydrogen peroxide) may be used. These cationic compounds are FDA approved and are used widely in wound dressings.

The present disclosure is not limited to particular polymer materials for use in filling the fiber tube or sleeve. Examples of biocompatible polymers include, but are not limited to, calcium phosphate, poly(lactic-co-glycolic) acid, polyanhydrides, polyvinylchloride (PVC), polyethylene (PE), polypropylene (PP), polymethylmetacrylate (PMMA), polystyrene (PS), polytetrafluoroethylene (PTFE), polyurethane (PU), polyamide (nylon), polyethylenterephthalate (PET), polyethersulfone (PES), polycarbonates (PC), polyetherimide (PEI) (See e.g., Pandey et al., IJPSR, 2016; Vol. 7(7): 2748-2755), polycaprolactone (PCL), or mineralized bone particles (MBP).

In some embodiments, polymerization of the biocompatible polymer occurs in situ. For example, in some embodiments, the delivery system comprises photocurable or photocrosslinkable polymers that are degradable or non-degradable. The photocrosslinking is not limited to UV and also includes visible, near IR (NIR), IR and other ranges. Photocurable or photocrosslinkable polymers can be synthesized or commercially obtained. In some embodiments, multifunctional monomers bearing cleavable linkage of the polymer are UV cured in the presence of a photoinitator (e.g., Irgacure 2959 (274 nm), or Darcocure (295 nm). The polymerizing unit may contain and not be limited to methacrylate, acrylate, epoxy units etc. Cleavable units include but are not limited to, acetal, hemiacetal, ester, carboxylate, carbonate, and thiol.

Carbon fibers are not UV transparent, which is challenging for using UV curing resins with carbon fiber patches. To solve this problem, cationic polymerization is useful because of continued dark polymerization after UV absorption. Examples include but are not limited to cationic photoinitators (e.g., aryl iodonium salts, triphenyl sulfonium, diazonium, ferrocenium etc.). Cationic polymerization allows for tighter control of the molecular weight compared to free radical polymerization and exhibits a very low shrink rate and provides robust implant stability.

Figure 2:
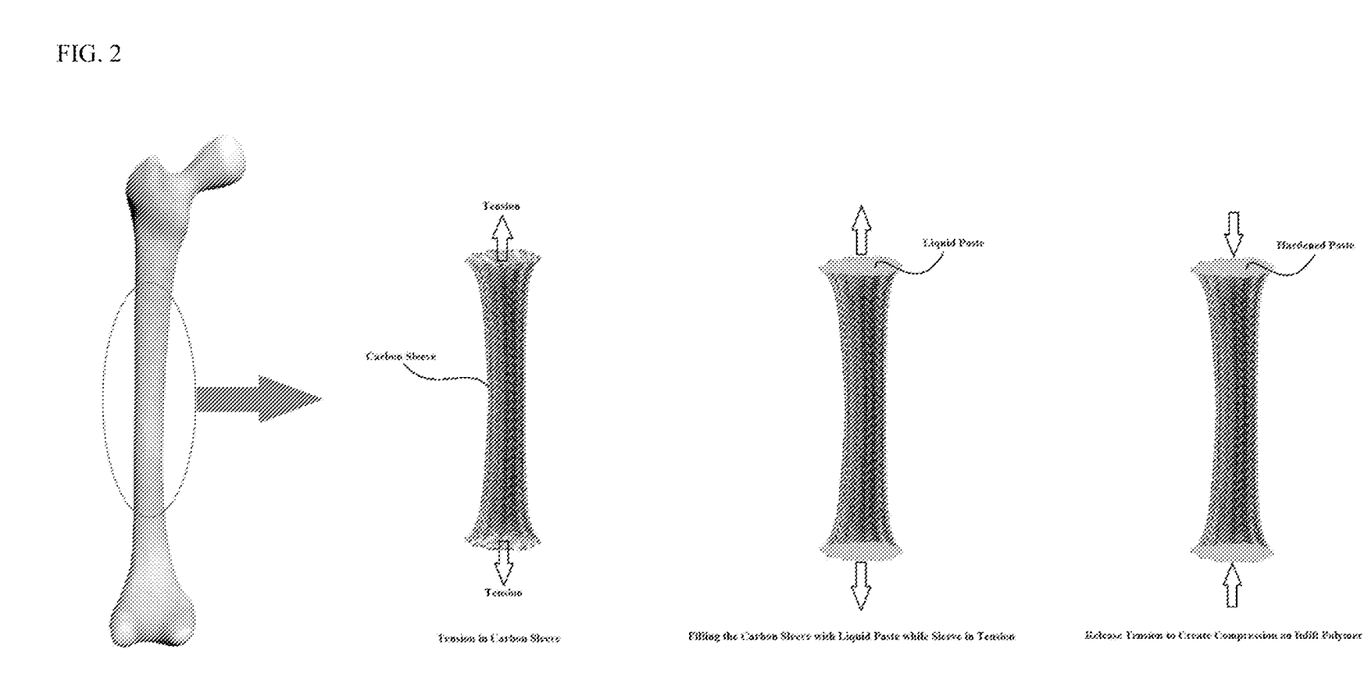
FIG. 2 shows exemplary precompression of infill material.

In some embodiments, polymer infill materials have high compression, but weak tension. Typically, the tensile strength of polymer fillers is about 10% to 20% of their compressive strength; therefore, in some embodiments, inner reinforcement is used for the fillers to create a balanced design. In some embodiments, in order to improve the tensile strength of the filler, the filler is pre-compressed before any load is applied. In this manner, the pre-compressive stresses negate the tensile stresses resulting from the applied loads due to shear and torsional forces, as shown in FIG. 2. The pre-compression is achieved by applying a tension force to the carbon fiber while the infill paste is in a liquid state and releasing that tension force as soon as the infill polymer material is set. The reaction from the release translates into a permanent compression force on the paste as shown in FIG. 2.

There are three types of stresses that the bone is subjected to after treatment: compressive stresses, tensile stresses due to bending and tensile stresses due to torsion. In some embodiments, the tensile stresses are compensated for either by pre-compression or by the use of an internal scaffold of carbon fiber, as shown in FIG. 3(b).

In some embodiments, the polymer is an expansive polymer that expands in the bone cavity, providing compressive stresses and aiding in bonding the polymer to the bone and/or fiber sleeve.

Figure 3:
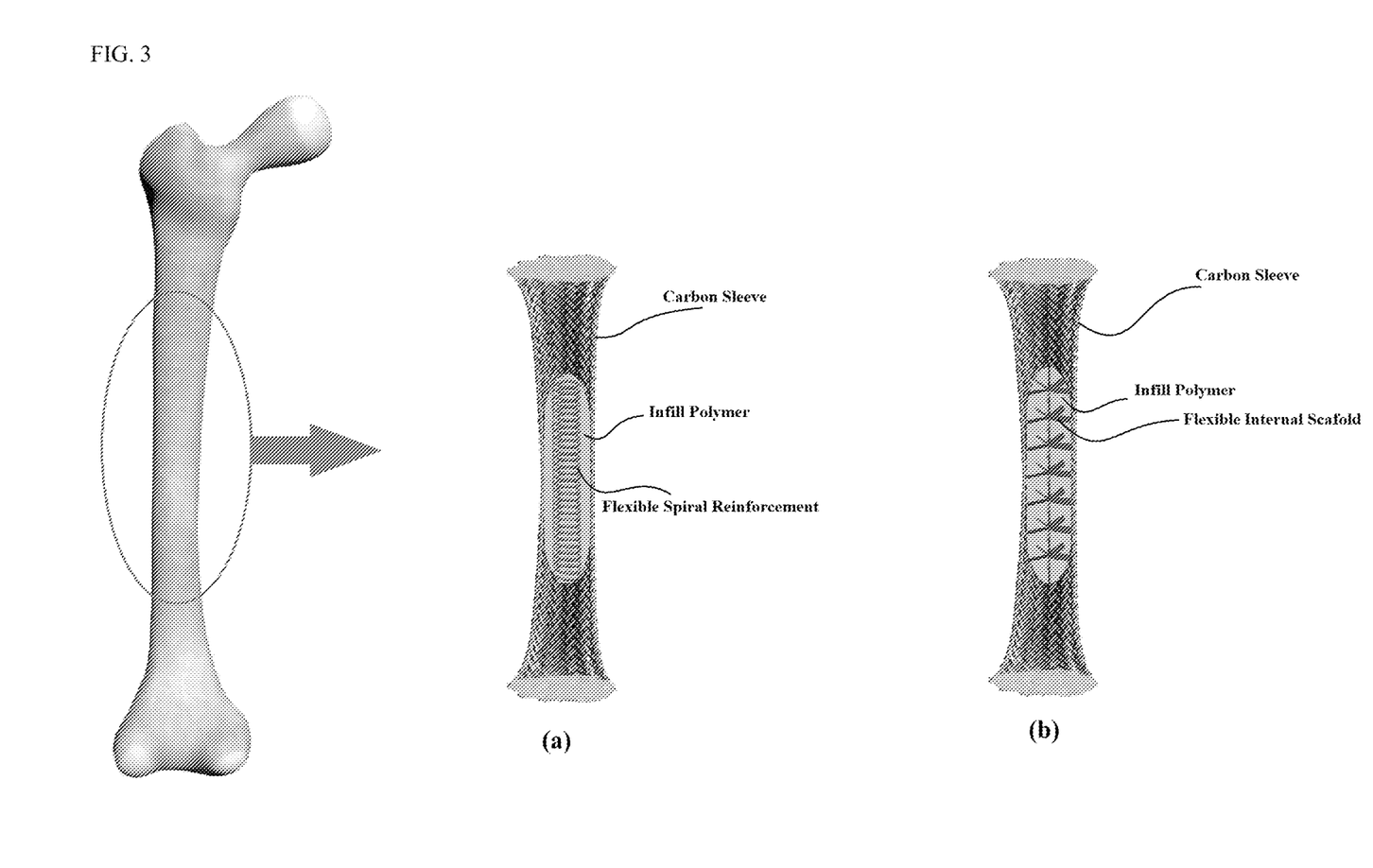
FIG. 3 shows internal carbon reinforcement in a carbon sleeve.

In some embodiments, an alternative to including internal scaffolding reinforcement in the carbon sleeve is to insert a flexible, spring like carbon fiber spiral reinforcement as shown in FIG. 3 (a) to increase the capacity of the infill material to resist tensile stresses developed as a result of shear and torsional forces, as shown in the figure.

In some embodiments, implants comprise small fibers mixed with the polymer prior to injection into the bone. Mixing small fibers (e.g., carbon fibers, carbon nanoparticles, etc.) with the polymer significantly enhances the tensile strength of the compound. In some embodiments, this eliminates the need for a carbon sleeve or membrane. In some embodiments, such implants are combined with carbon fiber sleeves, bags, or tubes.

In some embodiments, the fiber component and/or the biocompatible polymer comprise one or more additional components. For example, in some embodiments, drugs (e.g., antibiotics, agents that promote bone healing such as growth factor, or chemotherapeutic agents) or bone precursors (e.g., osteoblasts and/or osteoclasts) are incorporated into the carbon fiber or biocompatible polymer.

In some embodiments, fiber components (e.g., tubes) and/or biocompatible polymer components are designed to change properties with electrical, chemical, temperature, or UV stimulation. For example, in some embodiments, outside or intrinsic stimuli are used to adjust the mechanical properties of the fiber or polymer component and/or release a component (e.g., antibiotic) or soften the polymer for removal.

As described herein, in some embodiments, the compositions of the present disclosure are removable. For example, in some embodiments, an injectable delivery system comprising biocompatible gold nanoparticles are injected and heated using radio frequency waves (RF) or contain degradable crosslinkers that are labile to UV, thermal, organic solvents or enzymes that can be safely degraded and liquified are used. The depolymerized polymerized implant along with the carbon sleeve are then effectively removed from the medullary shaft of the bone.

In some embodiments, gold nanoparticles for implant removal are heated using shortwave RF fields, which is non-invasive to the human body, has full-body penetration, and has been extensively studied for in situ cancer ablation and drug delivery systems. In some embodiments gold nanoparticles (GNp) have a diameter of 1 nm-100 nm and are mixed within the monomer to obtain a homogeneous dispersion prior to polymerization. The gold nanoparticles may be used with or without surface modification. To depolymerize the implant, RF waves in the operating frequency (e.g., ranging between 13.56 MHz-50 GHz and an operating power of 200 W) are used. The gold nanoparticles are nontoxic to the body and are well tolerated. They have a low reticulo endothelial (RER) clearance rate and hence stay within the liquified polymer system for safe removal.

In some embodiments, removal methods utilize the incorporation of photolabile crosslinkers including but not limited to, 1,4-diacetylbenzene 1,4-bis(O-methacryloyl)dioxime and 1,3,5-triacetylbenzene 1,3,5-tris(O-methacryloyl) trioxime) mixed with the injectable polymer system. Such crosslinkers are UV depolymerized within the carbon sleeve and then are removed.

In some embodiments, the fiber tubes and biocompatible polymers are provided as a kit or system (e.g., comprising a fiber tube material described herein and optionally a biocompatible polymer). In some embodiments, kits and systems further comprise one or more components useful, necessary, or sufficient to perform the described methods (e.g., including but not limited to, guide wires, additional reinforcing materials, removal components, and the like).

The systems and method of the disclosure find use in the treatment of fractures in any bones with fractures amendable to treatment with the disclosed systems and kits. Examples include, but are not limited to, clavicle, radius, ulna, hip, femur, tibia, and fibula. The systems and methods described herein find use in the treatment of a variety of types of fractures including, but not limited to, stable fractures, open, compound fractures, transverse fractures, oblique fractures, and comminuted fractures.

The systems and methods described herein further find use in strengthening bones in subjects at an increased risk of fractures (e.g., subjects with overuse, injury, cancer, osteoporosis or other disorders). Thus, in subject embodiments, the systems and methods are used to prevent, rather than treat, fractures. In some embodiments, bone strengthening applications provide a permanent fix for weak bones.

The systems and methods described herein find use in the treatment and prevention of fractures in any number of subjects. In some embodiments, the subject is a human. In other embodiments, the subject is a non-human animal. For example, in some embodiments, the subject is an equine (e.g., racehorse) or companion animal (e.g., dog or cat), although additional subjects are specifically contemplated.

EXAMPLES

The following examples are included to demonstrate certain embodiments of the invention. It should be appreciated by those of skill in the art that the techniques disclosed in the examples which follow represent techniques discovered by the inventors to function well in the practice of the invention, and thus are considered to constitute certain aspects for its practice. However, those of skill in the art should, in light of the present disclosure, appreciate that many changes can be made in the specific embodiments which are disclosed and still obtain a like or similar result without departing from the spirit and scope of the invention.

Example 1—Fixation of a Fractured Humerus in a Human Patient

The following example describes treatment strategies for a fractured humerus involving a treatment method of embodiments of the present invention.

A 25 year old human male patient presents with a fractured humerus. The bone was broken in an automobile accident. He visits a physician and undergoes x-ray imaging. He is diagnosed with a compound fracture of the right humerus. The physician recommends minimally invasive fixation using an intramedullary carbon fiber tube. The patient is sedated and treated with a bone repair system described herein. During his follow up visit with his physician, the patient undergoes additional x-ray imaging which shows that the bone is healing. The patient continues to improve and regains full use of the right arm within 3 months. No side effects are reported.

Example 2—Reinforcement of a Hip Bone in a Patient with Osteoporosis

The following example describes treatment strategies for strengthening of a hip bone involving reinforcement with a carbon fiber tube of embodiments of the present invention.

A 71 year old woman is diagnosed with severe osteoporosis. A physician treats the woman with a bone strengthening repair system described herein. The patient continues to improve and is able to walk normally within 3 months. No side effects are reported.

Example 3—Fixation of Fractured Equine Tibia

The following example describes a treatment strategy for an equine with a fractured tibia involving implantation of a carbon fiber tube of embodiments of the present invention.

A 3 year old male racehorse presents with a weakness in the left foreleg. A veterinary surgeon diagnoses the horse with a fractured tibia. The surgeon repairs the bone with a bone repair system described herein. The horse continues to improve and is functioning normally at 4 months. No side effects are reported.

Example 4—Fixation of Fractured Equine Pelvis

The following example describes a treatment strategy for an equine with a fractured pelvis involving implantation of a carbon fiber tube of embodiments of the present invention.

A 5 year old female workhorse presents with lameness. A veterinary surgeon diagnoses the horse with a fractured pelvis. The surgeon treats the fracture with a bone repair system described herein. The horse continues to improve and is functioning normally at 6 months. No side effects are reported.

All publications and patents mentioned in the above specification are herein incorporated by reference as if expressly set forth herein. Various modifications and variations of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in relevant fields are intended to be within the scope of the invention.

What is claimed is:

1. A method of treating, stabilizing, or preventing a bone fracture or strengthening a bone, comprising:
   a. making at least a first hole and a second hole through said bone by drilling or laparoscopy;
      wherein a first of said holes is placed on a proximal side of said bone fracture and a second of said holes is on a distal side of said bone fracture;
   b. inserting a fiber tube in said first hole, wherein said inserting said fiber tube comprises the steps of:
      i. inserting said fiber tube in said first of said holes, and
      ii. drawing said fiber tube via a lead wire that exits said second of said holes;
      wherein said fiber tube is placed between said first and second holes;
      wherein said fiber tube comprises one or more surface modifications selected from the group consisting of electrochemical, chemical, thermal, discharge plasma, and radiation treatment;
      wherein said fiber tube is pre-impregnated with a resin system at a temperature below the physiological temperature and resin system polymerizes at physiological temperature after insertion of said fiber tube in said bone;
      wherein said fiber tube is removable;

wherein said fiber tube is configured to resist compressive, torsional, and shear forces when placed in a bone, conforms to the shape of a bone cavity in said bone, and is configured to retain tube shape after placement in said bone; and c. filling said fiber tube, said first hole, and said second hole with a biocompatible polymer;

wherein said biocompatible polymer is pre-compressed before filling, is an expansive polymer, and comprises a carbon fiber reinforcing component;

wherein said fiber tube and said biocompatible polymer further comprises one or more active agents selected from the group consisting of a drug, antimicrobial agent, antibiotic, bone healing promoting agent, chemotherapeutic agent, or bone precursor such as osteoblast or osteoclast;

wherein at least one physical property of said biocompatible polymer is altered by an external stimulus that is either electrical or thermal energy;

wherein said first hole and said second hole act as shear keys after being filled with the biocompatible polymer.

2. The method of claim 1, wherein said fiber tube is a carbon fiber tube, an ultrathin layer of carbon fabric, or a double layered bag comprising outer porous carbon fiber layer and inner non-porous carbon fiber layer.

3. The method of claim 1, wherein said surface modifications comprise antimicrobial agents selected from the group consisting of cationic groups such as quaternary ammonium compounds, metal-based antimicrobials such as silver or bismuth, polymer-based antimicrobials such as polyhexamethylene biguanide, and oxidizing agents such as hydrogen peroxide.

4. The method of claim 1, wherein said biocompatible polymer is selected from the group consisting of calcium phosphate, poly(lactic-co-glycolic) acid, polyanhydrides, polyvinylchloride (PVC), polyethylene (PE), polypropylene (PP), polymethylmetacrylate (PMMA), polystyrene (PS), polytetrafluoroethylene (PTFE), polyurethane (PU), polyamide (nylon), polyethylenterephthalate (PET), polyethersulfone (PES), polycarbonates (PC), polyetherimide (PEI), Polycaprolactone (PCL), and mineralized bone particles (MBP).

5. The method of claim 1, wherein said biocompatible polymer comprises a depolymerization agent selected from the group consisting of gold nanoparticles, photolabile crosslinkers, degradable crosslinkers such as 1,4-diacetylbenzene 1,4-bis(O-methacryloyl)dioxime and 1,3,5-triacetylbenzene 1,3,5-tris(O-methacryloyl)trioxime.

6. The method of claim 5, wherein said fiber tube is removed by exposing said gold nanoparticles to radiofrequency or said photolabile crosslinkers to UV light.

7. The method of claim 1, wherein said fracture is selected from the group consisting of stable fractures, open, compound fractures, transverse fractures, oblique fractures, and comminuted fractures.

8. The method of claim 1, wherein said fracture is in a bone selected from the group consisting of the clavicle, sternum, phalanges, metacarpals, radius, ulna, hip, femur, tibia, and fibula.

9. The method of claim 1, wherein said treating, stabilizing, or preventing a bone fracture or strengthening a bone is for human or non-human animal that has a bone injury, has increased risk of a bone fracture, has overuse condition, has cancer or osteoporosis.

* * * * *